United States Patent [19]

Haruta et al.

[11] Patent Number: 5,329,042

[45] Date of Patent: Jul. 12, 1994

[54] CYCLOHEXENE DERIVATIVE AND METHOD OF PRODUCING THE SAME

[75] Inventors: Junichi Haruta; Kazuhiko Sakuma; Akihiro Yasuda; Katsuyoshi Hara; Itsuo Uchida, all of Yokohama, Japan

[73] Assignee: Japan Tobacco Inc., Tokyo, Japan

[21] Appl. No.: 955,757

[22] PCT Filed: Apr. 24, 1992

[86] PCT No.: PCT/JP92/00537

§ 371 Date: Dec. 24, 1992

§ 102(e) Date: Dec. 24, 1992

[87] PCT Pub. No.: WO92/19582

PCT Pub. Date: Nov. 12, 1992

[30] Foreign Application Priority Data

Apr. 26, 1991 [JP] Japan .................. 3-188377
Apr. 26, 1991 [JP] Japan .................. 3-188378

[51] Int. Cl.[5] .......................................... C07C 205/00
[52] U.S. Cl. ................................. 560/125; 562/507
[58] Field of Search ....................... 560/125; 562/507

[56] References Cited

FOREIGN PATENT DOCUMENTS 0384380 8/1990 European Pat. Off. .
58-192845 11/1983 Japan .
3236397 10/1991 Japan .

OTHER PUBLICATIONS

Koichi Kojima et al, Chemical & Pharmaceutical Bulletin, vol. 33, No. 7 (1985) pp. 2750–2761.
Chem. Abstr. 100(11):81182u (1984) V. Meer et al, J. Econ. Econ. Entomol.
Chem. Abstr. 95:6890y (1981) K. C. Mathur et al, J. Chin. Chem. Soc., 29(3), 197–200 (1982).
Chem. Abstr. 97(25):215710v (1982) K. C. Mathur et al, J. Chin. Chem. Soc., 29(3), 197–200 (1982).
M. Ishizaki et al, Tetrahedron Letters, vol. 32, No. 48 (1991) pp. 7079–7082.
K. Sugita et al, Bulletin of the Chemical Society of Japan, vol. 44, No. 10 (1971).
Chem. Abstr. 66(13):54756g (1967), V. M. Andreev et al, Izv. Akad. Nauk, SSSR, 1966(8), 1410–16.
Chem. Abstr. 77(7):47912d (1972), K. C. Mathur et al, J. Chin. Chem. Soc. 29(3), 197–200 (1982).
Chem. Abstr. 84(9):59412y (1976) S. Jacques et al., Bull. Boc. Chem. Fr., (1975).
K. Tomioka et al Journal of the Chemical Society, Perkin Transactions 1, 1990, No. 2, pp. 426–428.

(List continued on next page.)

Primary Examiner—Paul J. Killos
Attorney, Agent, or Firm—Birch, Stewart, Kolasch & Birch

[57] ABSTRACT

Provided is a novel (1R, 2S)-1-acyl-2-carboxycyclohex-4-ene derivative represented by the following general formula [I], and its producing method,

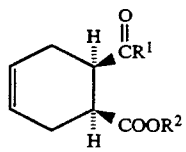

[I]

(where $R^1$ represents a hydrogen atom, a lower alkyl group, or substituted or unsubstituted aryl group, and $R^2$ represents a hydrogen atom, or a lower alkyl group). Also provided is a method of producing a (3S, 4R)-4-substituted-3-carboxycyclopentanone derivative represented by the following general formula [A],

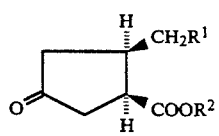

[A]

(where $R^1$ and $R^2$ are the same as those mentioned above).

17 Claims, No Drawings

OTHER PUBLICATIONS

Chem. Abstr. 65(9):13565g (1966) H. Christol et al, Bull. Soc. Chem. Fr., 1966(4), 1315–24.

C. A. Buehler et al, "Survey of Organic Syntheses" vol. 2 (1977), John Wiley & Sons (N.Y.) pp. 4, 5, 9, 499, 616–618.

Beckwith, A. et al. Tetrahedron Lett 33(34), 4975–8 1992.

Toone, et al. Tetrahedron Asymmetry 2(3) 207–22 1991.

Viktorova, N. M. et al Zh. Org. Khim. 8(5) 944–8 1972.

Zefirov, N. S. et al. Tetrahedron Lett (12)1091–4 1972.

Christol, H. et al. Bull. Soc. Chim. Fr., (8) 2535–41 1966.

CYCLOHEXENE DERIVATIVE AND METHOD OF PRODUCING THE SAME

TECHNICAL FIELD

The present invention relates to a method of producing a (3S, 4R)-4-substituted-3-carboxycyclopentanone derivative represented by the following formula [A] and used as a starting material for a TRH derivative useful in a remedy for treating a prolonged clouding of consciousness and spinal cerebellar denaturation disease,

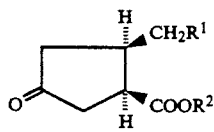

[A]

(where $R^1$ is a hydrogen atom, a lower alkyl group, or substituted or unsubstituted aryl group, and $R^2$ is a hydrogen atom or a lower alkyl group. The wedge shape full lines indicate bonds facing in an upward direction from the page, and the dotted lines indicate bonds facing in a downward direction into the page), and a method of producing a cyclohexene derivative, which can be an important intermediate in preparing a compound represented by the formula [A], for example, those represented by the following formulas [I], [VII], and [X],

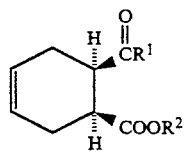

[I]

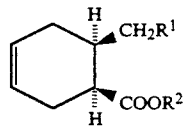

[VII]

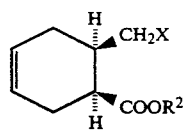

[X]

(where $R^1$ and $R^2$ represent the same as those of the above, and X is a halogen atom).

Prior Art

TRH (thyrotropin releasing hormone) is a tripeptide of L-pyroglutamyl-L-histidyl-L-proline amide (pGlu-His-Pro-NH$_2$), and synthesized in the hypothalamus in the brain. TRH acts on the anterior lobe of the hypophysis to induce secretion of thyroid-stimulating hormone (TSH), which stimulate secretion of thyroid hormone, and secretion of luteinizing hormone. It is also known that in addition to the TSH secretion activating function, TRH is a useful remedy for prolonged clouding of consciousness and spinal cerebellar denaturation disease, caused by brain function disorder. Prior to the present invention, we proposed a novel TRH derivative represented by the following general formula [B] (See Published Unexamined Japanese Patent Application (PUJPA) No. 3-236397),

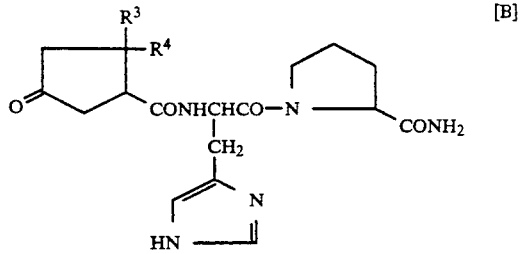

[B]

(where each of $R^3$ and $R^4$ represents a hydrogen atom, a lower alkyl group, or phenyl group, and they may differ from each other, or be the same except that $R^3$ and $R^4$ must not be hydrogen atoms at the same time).

A TRH derivative represented by formula [B] can be obtained from an ordinary peptide forming reaction between a cyclopentanone derivative or a reactive derivative thereof, represented by the following general formula [A'], and a dipeptide compound or a salt thereof, represented by the following general formula [C],

[A']

(where $R^3$ and $R^4$ represent the same as those of the above)

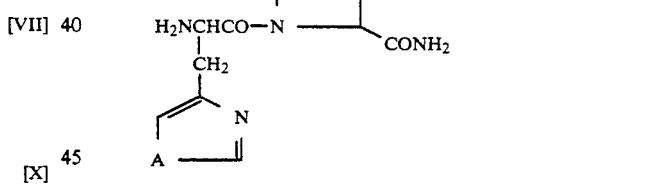

[C]

(where A represents an imino group, and may be protected or not protected).

Of all the possible cyclopentanone derivatives represented by formula [A'], some types of stereoisomers and optical isomers can be prepared, for example, by a method including the following reactions (See Chem. Pharm. Bull., 33(7)2750-2761(1985)),

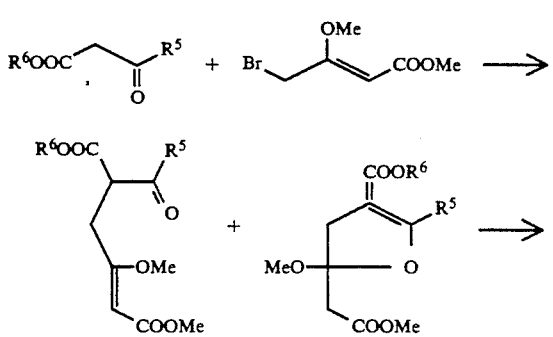

-continued

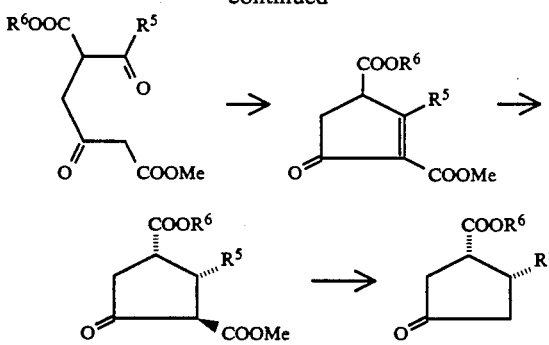

($R^5$ is a methyl group, and $R^6$ is a benzyl group).

Based on the known technique described above, we also prepared a cyclopentanone derivative [A'] in the process of completion of our prior invention (PUJPA No. 3-236397), as a starting material of the invention.

However, as is obvious from its chemical structural formula, there are stereoisomers including cis-types and trans-types at positions 3 and 4 in a cyclopentanone derivative [A'], and in addition to these, there are optical isomers for each of the cis-, and trans-types in positions 3 and 4.

Therefore, it is difficult to selectively synthesize an optically active compound having a specific configuration (substituting groups of cyclopentanone at positions 3 and 4 have a cis-configuration), and a (3S, 4R) configuration at the same time. Thus, not only is the yield of the target compound low, but the handling of the products, for example physical and chemical separation of isomers, is complex.

DISCLOSURE OF THE INVENTION

The present inventors made intensive studies to solve the drawback of the conventional technique such as described above, and focused on a (1R, 2S)-2-methoxycarbonylhex-4-ene-1-carboxylic acid represented by formula [XII'].

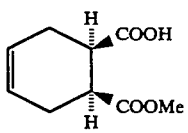
[XII']

Specifically, a method of preparing a compound [XII'] by an enzymatic process has been established recently, and therefore the compound can now be synthesized in a great amount at an inexpensive cost. The authors of the invention used this compound as a starting material to develop a method of preparing (3S, 4R)-4-substituted-3-carboxycyclopentanone derivative [A]. The authors discovered two effective ways of preparing the derivative. One includes, as shown in the flow diagram 1 (production method 1), the steps of selectively replacing the carboxyl group at the position 1 of the compound [XII] with an acyl group, and replacing this acyl group with an alkyl group or a benzyl group. The other includes, as shown in the flow diagram 2 (production method 2), the steps of converting the compound [XII] to a γ-lactone derivative, opening the γ-lactone ring by halogenating the derivative in an inert solvent such as methylene chloride, reducing the halogenated methyl group at the position 6 to a methyl, opening the cyclohexanene ring by oxidation, and closing the opened ring by use of an acid anhydride.

A purpose of the invention is to provide a method of producing the (3S, 4R)-4-substituted-3-carboxycyclopentanone derivative represented by the following general formula [A], characterized by oxidation of the (1S)-cis-6-substituted-1-carboxycyclohex-3-ene derivative represented by the following general formula [VII] into a diacid represented by the following general formula [XI], and cyclization of this diacid in the presence of an acid anhydride, followed by decarbonation.

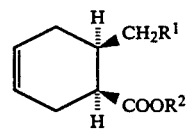
[VII]

(where $R^1$ and $R^2$ are the same as those mentioned above)

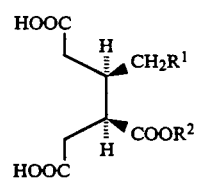
[XI]

(where $R^1$ and $R^2$ are the same as those mentioned above)

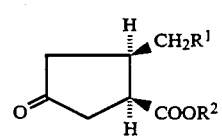
[A]

(where $R^1$ and $R^2$ are the same as those mentioned above)

Another purpose of the invention is to provide a method of producing the (1S)-cis-6-substituted-1-carboxycyclohex-3-ene derivative represented by the following general formula [VII], characterized by reducing the (1R, 2S)-1-acyl-2-carboxycyclohex-4-ene derivative represented by the following general formula [I].

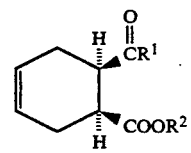
[I]

(where $R^1$ and $R^2$ are the same as those mentioned above)

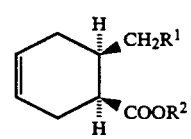
[VII]

(where $R^1$ and $R^2$ are the same as those mentioned above)

Another purpose of the invention is to provide a method of producing the (1S)-cis-6-substituted-1-carboxycyclohex-3-ene derivative set forth above, characterized by having the (1R, 2S)-1-acyl-2-carboxycyclohex-4-ene derivative represented by the following general formula [I] react with arylsulfonylhydrazine to obtain a hydrazone derivative represented by the following general formula [VIII], followed by reduction.

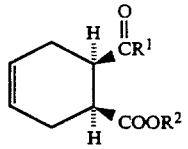

[I]

(where $R^1$ and $R^2$ are the same as those mentioned above)

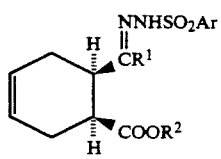

[VIII]

(where $R^1$ and $R^2$ are the same as those mentioned above, Ar is a substituted or unsubstituted aryl group)

Another purpose of the invention is to provide a method of producing the (1S, 2S)-1-aralkyl-2-carboxycyclohex-4-ene derivative represented by the following general formula [VII''], characterized by reducing the (1R, 2S)-1-arylcarbonyl-2-carboxycyclohex-4-ene derivative represented by the following general formula [I'''] with a metal hydride compound,

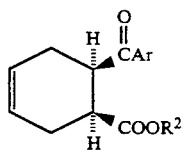

[I''']

(where $R^2$ and Ar are the same as those mentioned above)

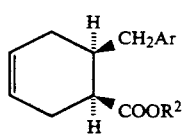

[VII'']

(where $R^2$ and Ar are the same as those mentioned above).

Another purpose of the invention is to provide a novel (1R, 2S)-1-acyl-2-carboxycyclohex-4-ene derivative represented by the following general formula [I],

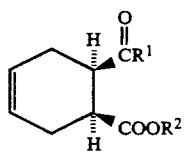

[I]

(where $R^1$ and $R^2$ are the same as those mentioned above).

Another purpose of the invention is to provide a method of producing a (1R, 2S)-1-acyl-2-carboxycyclohex-4-ene derivative represented by the general formula [I'] below, characterized by having a (1R, 2S)-1-haloformyl-2-carboxycyclohex-4-ene derivative represented by the following general formula [II] react with:

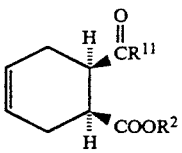

[I']

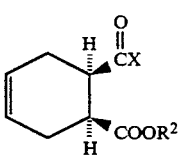

[II]

(where $R^2$ and X are the same as those mentioned above)

1) Grignard reagent represented by the following general formula [III] in the presence of copper catalyst,

$R^{11}MgX'$   [III]

(where $R^{11}$ represents a lower alkyl group, or a substituted or unsubstituted aryl group. X' is a halogen atom, and may be the same as or different from that represented by X mentioned before), or 2) copper ate complex represented by the following general formula [IV]

$R^{11}{}_2CuLi$   [IV]

(where $R^{11}$ is the same as that mentioned above) or the following general formula [V]

$R^{11}{}_nCu(CN)Li_n$   [V]

(where $R^{11}$ is the same as that mentioned above, and n is integer of 1 or 2).

Another purpose of the invention is to provide a method of producing a compound represented by the above formula [I'] by use of a copper catalyst such as CuX'', Cu, or CuCN (where X'' is a halogen atom, and X and X' may be the same or different from each other).

Another purpose of the invention is to provide a method of producing the (1R, 2S)-1-formyl-2-carboxycyclohex-4-ene derivative represented by the following general formula [I''], characterized by reducing the (1R, 2S)-1-haloformyl-2-carboxycyclohex-4-ene derivative represented by the following general formula [II] with a reducing agent selected from metal hydride compounds or metal hydride complex compounds,

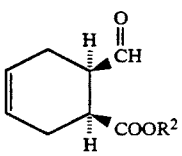

[I'']

(where $R^2$ is the same as those mentioned above)

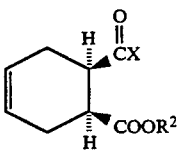

[II]

(where $R^2$ and X are the same as those mentioned above).

Another purpose of the invention is to provide a method of producing a compound represented by the above formula [I''] by use of n-Bu$_3$SnH, Et$_3$SiH, NaBH$_4$, NaBH$_3$CN, or LiAlH$_4$ as the reducing agent.

Another purpose of the invention is to provide a method of producing a (1S, 6R)-6-halomethyl-1-carboxycyclohex-3-ene derivative represented by the general formula [X'] below, characterized by having (3aR, 7aS)-1,3,3a,4,7,7a-hexahydroisobenzofuran-1-one represented by the following formula [IX] react with a halogenating agent in an inert solvent, followed by treatment using a lower alcohol represented by $R^2$OH or water; or react with a halogenating agent in a lower alcohol solvent, followed by hydrolysis if necessary,

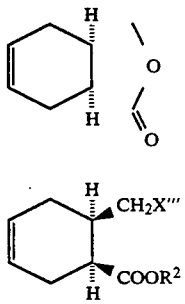

[IX]

[X']

(where $R^2$ is the same as that mentioned above, and X''' represents a halogen atom, and may be the same as the above X, or different from each other).

Another purpose of the invention is to provide a method of producing a (1S, 6R)-6-methyl-1-carboxycyclohex-3-ene derivative represented by the general formula [VII'] below, characterized by having a (1S, 6R)-6-halomethyl-1-carboxycyclohex-3-ene derivative represented by the following general formula [X'] react with a metal hydride complex compound.

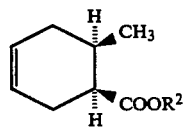

[VII']

(where $R^2$ is the same as that mentioned above),

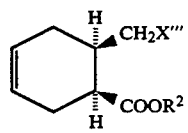

[X']

(where $R^2$ and X''' are the same as those mentioned above).

The present invention will now be described in further detail with reference to flow diagrams 1 and 2. According to the invention, there can be effectively obtained the final target compound [A] or [A'] having a desired configuration without being epimerized, from an inexpensive known compound represented by formula [XII] as a starting material.

In the flow diagram 1 and 2, $R^1$ represents a hydrogen atom, a lower alkyl group, or a substituted or unsubstituted aryl group, $R^2$ represents a hydrogen atom or a lower alkyl group, $R^{11}$ represents a lower alkyl group, or a substituted or unsubstituted aryl group, each of X, X', X'', and X''' represents a halogen atom (X, X' X'' and X''' may be the same, or different from each other), Ar is a substituted or unsubstituted aryl group, Ac is an acetyl group, and Tos is a paratoluenesulfonyl group.

What is meant by "lower alkyl group" is an alkyl group having a carbon number of 1–4, and which may be branched, and some of the examples thereof are a methyl group, ethyl group, propyl group, isopropyl group, butyl group, isobutyl group, sec-butyl group, and tert-butyl group.

Some of the examples of the "halogen atom" are a fluorine atom, chlorine atom, bromine atom, and iodine atom.

Some of the examples of the "aryl group which may be substituted" are a phenyl group, biphenyl group, naphthyl group, or the like which may contain a plurality of substituting groups selected from the abovelisted lower alkyl groups, halogen atoms, lower alkoxy groups such as methoxy, ethoxy, propoxy, isopropoxy, n-butoxy, sec-butoxy, tert-butoxy, and the like, nitro groups, and acyl groups such as acetyl, propionyl, butyryl, benzoyl and the like.

The "halogenating agent" set forth in the flow diagram 1 is SOCl$_2$, (COCl)$_2$, PCl$_5$, or the like.

The "halogenating agent" set forth in the flow diagram 2 is BBr$_3$, BCl$_3$, BI$_3$, Me$_3$SiI, Me$_3$SiBr, or the like.

The "metal hydride complex compound" is NaBH$_4$, LiAlH$_4$, NaBH$_3$CN, or the like.

The "metal hydride compound" is n-Bu$_3$SnH, Et$_3$SiH, BH$_3$, AlH$_3$, or the like, and preferable examples are n-Bu$_3$SnH, Et$_3$SiH, and the like.

The "acid anhydride" is acetic anhydride, propionic anhydride, phthalic anhydride, fumaric anhydride, or the like.

The "arylsulfonylhydrazine (NH$_2$NHSO$_2$Ar)" is phenylsulfonylhydrazine, paratoluenesulfonylhydrazine, mesitylsulfonylhydrazine, or the like.

The "copper catalyst (CuX'')" is CuI, CuBr, CuCl, Cu, CuCN, or the like.

The "Grignard reagent ($R^{11}$MgX')" is methylmagnesium bromide, ethylmagnesium bromide, propylmagnesium bromide, isopropylmagnesium bromide, butylmagnesium bromide, isobutylmagnesium bromide, sec-butylmagnesium bromide, tert-butylmagnesium bromide, phenylmagnesium bromide, or the like.

The "copper ate complex ($R^{11}_2$CuLi, $R^{11}_n$Cu(CN)-Li$_n$ (where $R^{11}$ is the same as that mentioned above, and n is an integer of 1 or 2)" is lithium dialkylcuprate, litium cyanomethylcuprate, or the like.

The "inert solvent" is dichloromethane, chloroform, 1,2-dichloroethane, or the like.

Flow Diagram 1 (Preparation Method 1)
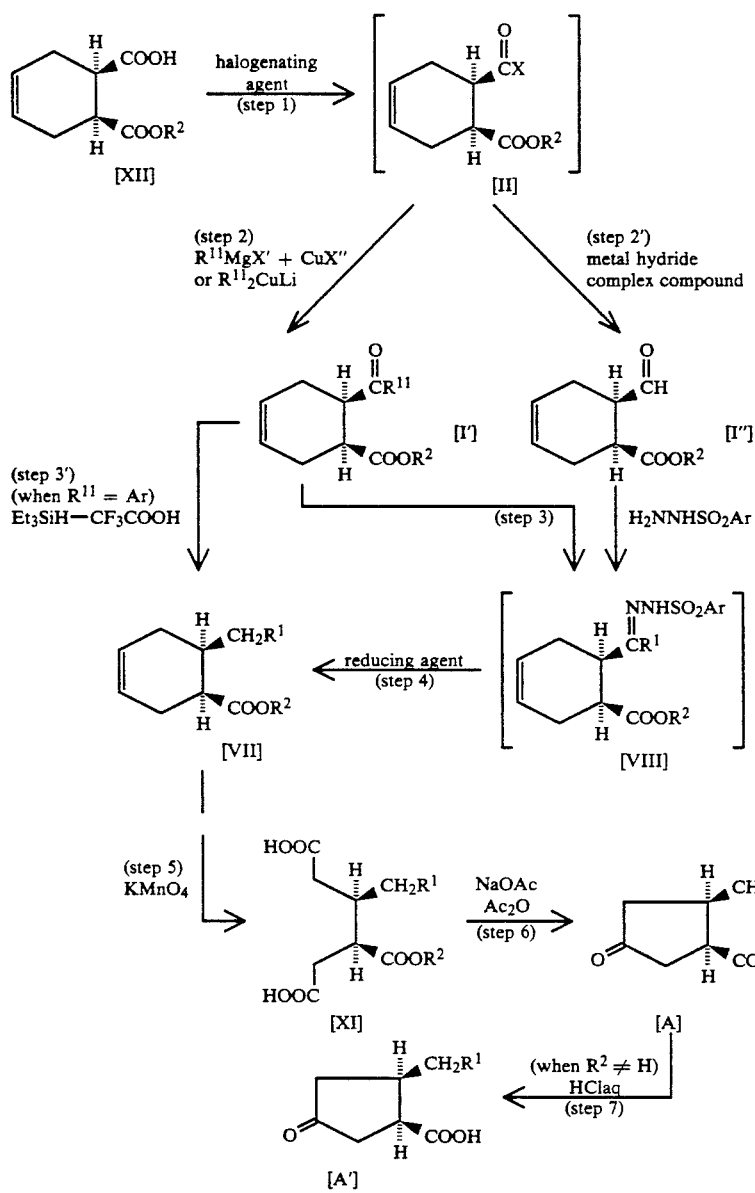
Flow Diagram 2 (Preparation Method 2)
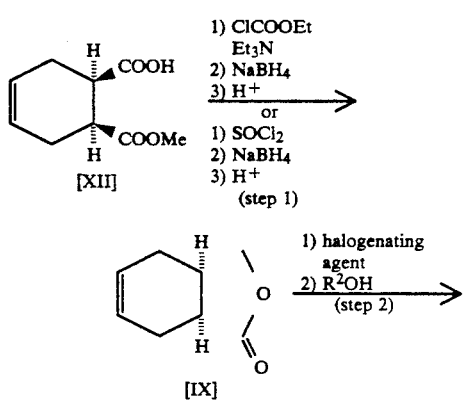
-continued
Flow Diagram 2 (Preparation Method 2)
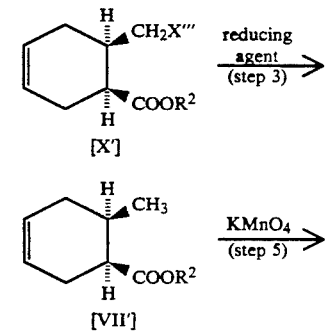

-continued
Flow Diagram 2 (Preparation Method 2)

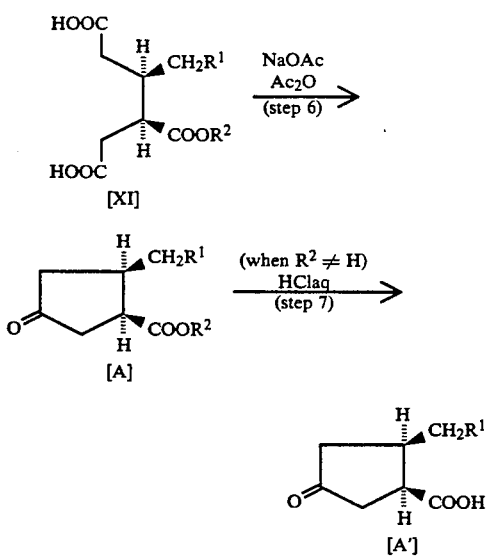

The steps in the production method 1 will now be described with reference to flow diagram 1.

Production Method 1
Step 1
A compound [XII] for example, (1R, 2S)-2-methoxycarbonylcyclohex-4-ene-1-carboxylic acid, and a halogenating agent such as thionyl chloride or oxalylchloride are dissolved in an inert solvent such as benzene as to have them react with each other under reflux or room temperature, thereby obtaining a haloformyl compound [II]. The obtained compound [II] may be isolated, or the resultant may proceed to step 2, or 2' without isolating the compound [II] therefrom.

The reaction involved in the above process is known, and is described by T. Wakamatsu et al. in Journal of Organic Chemistry 50, 108 (1985). The starting material, (1R, 2S)-2-methoxycarbonylcyclohex-4-ene-1-carboxylic acid, can be produced by an established production method using the enzymatic process as mentioned before (See S. Kobayashi et al. Chem. Pharm. Bull., 38,355, (1990)), and therefore high-purity (1R, 2S)-compound can be obtained easily at an inexpensive cost.

Step 2
The reaction involved in this step is conversion of the haloformyl derivative [II] obtained in step 1 to an acyl compound [I'], which is a novel compound.

The compound [II] obtained in step 1 described above is dissolved in an inert solvent such as benzene or tetrahydrofuran (THF), and is reacted by the following method 1) or 2), so as to obtain a compound [I'].

1) The compound [II] is to be reacted with a Grignard reagent represented by formula $R^{11}MgX'$ ($R^{11}$, and $X'$ are the same as those mentioned above) in the presence of copper catalyst $CuX''$ ($X''$ is a halogen atom, and X and $X'$ may be the same or different) (e.g., CuI, CuBr, CuCl, preferably CuI), Cu, and CuCN.

2) The compound [II] is to be reacted with a copper ate complex represented by formula $R^{11}{}_2CuLi$ or $R^{11}{}_nCu(CN)Li_n$ ($R^{11}$, and n are the same as those mentioned above).

It should be noted that $R^{11}{}_2CuLi$ can be easily prepared by, for example, adding lithium to an alkyl halide to convert it to alkyllithium, followed by addition of a cuprous halide.

What is of significance in this step is the use of a combination Grinard reagent-copper catalyst such as $MeMgBr$-CuI, or a copper ate complex such as $Me_2$-CuLi or $Me_nCu(CN)Li_n$ (n is the same as that mentioned above) as an alkylating agent. For example, in the case where only MeMgBr is used, epimerization occurs during the reaction, creating a large amount of trans isomers of the compound [I'], or an alcohol form due to further reaction as a by-product. When a copper catalyst is used along with MeMgBr, the side reactions of this type can be suppressed.

As described, by following the above reaction steps, a high yield of the compound [I'] having the desired configuration can be obtained.

Step 2'
When the formyl compound [I''], which is a compound [I] in which $R^1$ is a hydrogen atom is desired, the compound [II] as described above is dissolved in an inert solvent such as benzene, and made to react with a metal hydride (for example, n-Bu$_3$SnH, Et$_3$SiH, BH$_3$, or AlH$_3$, preferably n-Bu$_3$SnH or Et$_3$SiH) or reducing agent such as a metal hydride complex compound (for example, NaBH$_4$, LiAlH$_4$, NaBH$_3$CN) to reduce the haloformyl group of the compound [II], thereby obtaining the compound [II]. When n-Bu$_3$SnH is used as a reducing agent, a catalytic amount of Pd complex (Pd complex having a valence of 0, for example, tetrakis(triphenylphosphine)palladium(0), i.e. Pd$_2$(PPh$_3$)$_4$, tri(-dibenzylideneacetone)palladium(0), i.e. Pd$_2$(OBA)$_3$.CHCl$_3$), or Pd-C (palladium carbon) should preferably be used as well for a better result.

When the compound in which $R^2$ in the compound [I'] or [I''] obtained by means of step 2 or 2' is a hydrogen atom is desired, it can be obtained easily by hydrolyzing the ester group of the compound [I'] or [I''] by use of a known technique.

Step 3
This step is so-called a pre-process for the following reducing step in which only the acyl group of the compound [I'] or [I''] is selectively reduced.

The compound [I'] or [I''] obtained in step 2 or 2' is dissolved in a solvent such as methanol, and reacted with an arylsulfonylhydrazine such as tosylhydrazine to obtain a hydrazone derivative [VIII].

The compound [VIII] has a structure in which the acyl moiety of the compound [I'] or [I''] is converted to a hydrazone derivative. Thus, in the next step, only this converted moiety is reduced selectively and preferentially.

Before proceeding to the next step, the compound [VIII] may be isolated from the mixture, or the compound [VIII] obtained by concentration of the mixture to dryness may be used in step 4 without isolation.

Step 3'
When $R^{11}$ of the compound [I'] is an aryl group, according to the present step, the compound [I'] can be converted directly to the compound [VII] without undergoing a hydrazone derivative [VIII]. Specifically, triethylsilyl hydride (Et$_3$SiH) is treated with a compound [I'] in trifluoroacetic acid at room temperature or under heating to obtain the compound [VII].

Step 4
A polar solvent such as dimethylformamide or sulfolane is added to the concentrated and dried compound [VIII] obtained in step 3. Further, if necessary, cyclohexane or the like should be added. Then, preferably under an acidic condition, a reducing agent such as a metal hydride complex compound (for example, NaBH$_4$, LiAlH$_4$, NaBH$_3$CN, most preferably NaBH$_3$CN) is added gradually, and the mixture is reacted, preferably under a heating condition, to obtain the compound [VII].

Step 5

Potassium permanganate, a reducing agent, is dissolved in an appropriate amount of water, and an organic solvent such as benzene is added thereto. Then, a compound [VII] is added to the mixture while cooling with ice in the presence of a catalytic amount of a phase transfer catalyst such as tetrabutylammonium bromide (Bu$_4$NBr), and the resultant mixture is stirred at room temperature for several hours. The oxidative ring-opening reaction of the compound [VII] occurs to give a dicarboxylic compound [XI].

Step 6

The compound [XI] obtained in step 5 and sodium acetate are added to an appropriate amount of acetic anhydride, and the mixture is subjected to reflux so as to obtain the final target compound [A] through ring-forming and decarbonation of the compound [XI]. If necessary, the ester group of the compound [A] is hydrolyzed in the next step 7.

Step 7

This step involves a regular ester hydrolysis reaction, and the reaction can be easily carried out by a general method. For example, a compound [A] is added to an acid solution such as a hydrochloric acid solution, and the solution is refluxed. Then, the compound [A] is hydrolyzed to obtain the target compound [A'] in which R$^2$ is a hydrogen atom.

The steps involved in the production method 2 will now be described with reference to the flow diagram 2.

Production Method 2

Step 1

A compound [XII] is dissolved in an organic solvent such as tetrahydrofuran (THF) in an inert gas atmosphere, and an appropriate amount of a base (e.g., triethylamine) is added to the solution while cooling with ice. Then, ethyl chloroformate dissolved in an organic solvent such as THF is added to the mixture, and stirred while cooling with ice. After the obtained triethylamine hydrochloride is filtered off, a metal hydride complex compound (for example, NaBH$_4$, LiAlH$_4$, or NaBH$_3$CN) is added to the filtrate, which is stirred at room temperature for several hours. Next, an acid such as hydrochloric acid is added to the reaction solution to adjust the pH of the solution to 4–5, and the solvent, THF is distilled off under a reduced pressure. The residue is extracted with ethyl acetate or the like. Then, the extract is concentrated and the residue is dissolved in an organic solvent such as toluene. To this solution, an acid such as tosyl acid, hydrochloric acid, or sulfuric acid is added, and the reaction is carried out at room temperature for several hours, thereby obtaining a compound [IX].

In the meantime, the compound [IX] can be easily prepared by haloformylation of a compound [XII] according to step 1 of production method 1, followed by reducing the haloformyl compound with an appropriate reducing agent. Specifically, a compound [II] is dissolved in tetrahydrofuran (THF), dimethylformamide (DMF), or the like, and reacted with a metal hydride complex compound (NaBH$_4$, LiBH$_4$, LiEt$_3$BH, or the like, preferably NaBH 4 ) at a temperature in a range between −78° C. and room temperature, preferably at −40° C. for several hours. The resultant is subjected to a post-treatment similar to the above, and thus a compound [IX] is obtained.

It should be noted that the above-mentioned two reactions are carried out by the methods set forth in S. Kobayashi et al., Tetrahedron Lett., 31,1577 (1990), and H. J. Gais et al., Liebigs Ann. Chem. 687 (1986).

Step 2

In an inert gas atmosphere, e.g. nitrogen gas, the above-mentioned γ-lactone derivitive [IX] is dissolved in an inert solvent such as dichloromethane, chloroform, or 1,2-dichloroethane. Then, a halogenating agent (for example, boron tribromide (BBr$_3$), borontrichloride (BCl$_3$), boron triiodide (BI$_3$), iodotrimethylsilane (Me$_3$SiI), or bromotrimethylsilane (Me$_3$SiBr), preferably BBr$_3$) dissolved in a solvent such as dichloromethane is added dropwise, and stirred for about a whole day. When the reaction is completed, a lower alcohol represented by R$^2$OH (where R$^2$ is a lower alkyl group) such as methanol or ethanol is added, and the mixture can be further reacted to give the target compound, (1S, 6R)-6-halomethyl-1carboxycyclohex-3-ene derivative [X'].

The target compound [X'] ((1S, 6R)-6-halomethyl-carboxycyclohex-3-ene derivative) can be also obtained by treating a compound [IX] dissolved in a lower alcohol (R$^2$OH) such as methanol with a halogenating agent such as HBr or HI gas at a temperature of −20° C. to 40° C., preferably, room temperature.

Step 3

The compound [X'] obtained in the above step is dissolved in an inert solvent such as cyclohexane or hexane, and a prepared solution obtained by dissolving a metal hydride complex compound (for example, NaBH$_4$, LiAlH$_4$, or NaBH$_3$CN) in a polar organic solvent (for example, dimethylformamide, sulfolane, dimethylsulfoxide, or dimethylacetamide) is gradually added to the above compound [X'] solution, followed by stirring, preferably under heating. Thus, a (1S, 6R)-6-methyl-1-carboxycyclohex-3-ene derivative [VII'] is obtained.

The obtained compound [VII'] can be transformed into a compound [A] or [A'] by an operation similar to that of the steps from 5 to 7 illustrated in the flow diagram 1.

BEST MODE FOR CARRYING OUT THE INVENTION

Examples and reference examples of the invention will now be described in detail. It should be noted here that the invention is not limited to the following examples.

In the description, the following abbreviations will be used.

$^1$H-NMR: proton nuclear magnetic resonance spectrum

CI-MS: chemical ionization mass spectrum bp: boiling point mp: melting point

[α]$_D$: specific rotatory power

EXAMPLE 1

(1S, 2R)-2-formyl-1-methoxycarbonylcyclohex-4-ene

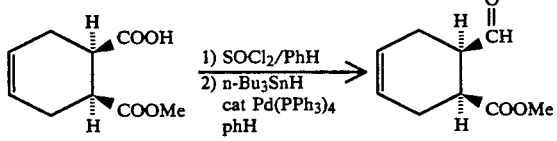

20 g of (1R, 2S)-2-methoxycarbonylcyclohex-4-ene-1-carboxylic acid and 15.9 ml of thionyl chloride were dissolved in 100 ml of dry benzene, and the mixture was refluxed for two hours. The solution was then cooled down to room temperature, and concentrated. To the residue, 50 ml of dry benzene was added in a nitrogen stream, and a catalytic amount (1.26 g) of tetrakis(triphenylphosphine)palladium (O) is further added. Then, 32.2 ml of tributyltin hydride was added dropwise over a period of 15 minutes. Thereafter, the solution was stirred for one hour at room temperature, and the mixture was concentrated. To the residue, 200 ml of n-pentane is added, and the resulting precipitate was filtered off. The filtrate was concentrated, and 80 ml of acetonitrile was added to the residue. The mixture was washed with hexane, and the acetonitrile layer was concentrated. To the residue was added 120 ml of diethylether, and a potassium fluoride solution was then added to the mixture, which was stirred for 5 minutes. The resulting precipitate was filtered off, and the water layer was extracted with ether. The ether layer was washed with saturated sodium hydrogencarbonate solution, dried over anhydrous magnesium sulfate, and concentrated. The residue was purified by distillation under a reduced pressure to give 15.4 g of the titled compound.

bp: 88°-90° C./0.6 mmHg
$[\alpha]^{23}D$: +25.9° (C=1.42, CHCl₃)
CI-MS m/z: 169 (M+1)+
$^1$H-NMR(CDCl₃)δppm: 2.25–2.62 (4H, m), 2.85–3.11 (2H, m), 3.70 (3H, s), 5.60–5.79 (2H, m)

EXAMPLE 2

(1S, 6R)-6-methyl-1-methoxycarbonylcyclohex-3-ene

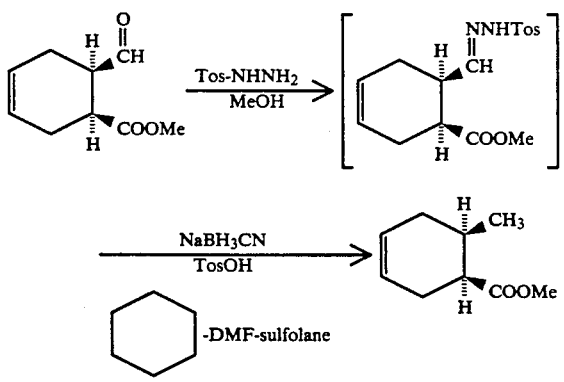

14 g of (1S, 2R)-2-formyl-1-methoxycarbonylcyclohex-4-ene was dissolved in 40 ml of methanol, and 15.5 g of tosylhydrazine was added while cooling the mixture by ice. The mixture was stirred for 3 hours at room temperature, and then concentrated. To the residue were added 125 ml of dimethylformamide, 125 ml of sulfolane, 3.2 g of p-toluenesulfonic acid monohydrate, and 125 ml of cyclohexane, and 20.9 g of sodium cyanoborohydride (NaBH₃CN) was gradually added while cooling the mixture by ice. The mixture was stirred for 3 hours at 100° C., and cooled down to room temperature. 300 ml of water was added to the mixture to separate the cyclohexane layer, and the water layer was extracted by cyclohexane. The cyclohexane layer was washed with a small amount of brine, and after drying over anhydrous magnesium sulfate, cyclohexane was distilled off under atmospheric pressure. The residue was purified by distillation under a reduced pressure to give 5.19 g of a mixture of the titled compound and 6% of the trans-isomer.

bp: 92° C./25 mmHg
$[\alpha]^{23}D$: +33.5° (c=1.56, CHCl₃)
CI-MS m/z: 155 (M+1)+
$^1$H-NMR(CDCl₃)δppm: 0.91 (3H, d, J=7.1Hz), 1.81–1.95 (1H, m), 2.16–2.42 (4H, m), 2.62–2.72 (1H, m), 3.68 (3H, s), 5.54–5.71 (2H, m)

EXAMPLE 3

(3S, 4R)-3-methoxycarbonyl-4-methylhexane dicarboxylic acid

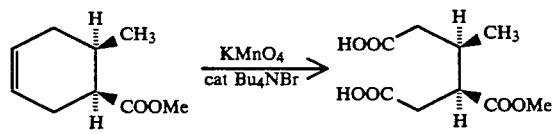

18.5 g of potassium permanganate and 70 ml of benzene were added to 200 ml of water. While cooling the mixture by ice, 1.88 g of tetrabutylammonium bromide and 4.5 g of (1S, 6R)-6-methyl-1-methoxycarbonylcyclohex-3-ene were added. The mixture was stirred for 2 hours at room temperature. Then, 5 g of sodium hydrogen sulfite was added to the reaction mixture, and after filtration of the precipitate, the filtrate was concentrated into half of its original volume. The concentrated mixture was washed with chloroform, and to the water layer was added concentrated hydrochloric acid such as to have a pH of 2. The water layer was extracted by a mixed solvent of ethyl acetate - tetrahydrofuran (1:1). The organic layer was dried over anhydrous magnesium sulfate and concentrated to dryness. The residue was recrystallized from 1,2-dichloroethane-hexane to give 4.8 g of the titled compound as white crystal.

mp: 98° C.
$[\alpha]^{23}D$: +23.9° (c=1.05, MeOH)
CI-MS m/z: 219 (M+1)+
$^1$H-NMR(CDCl₃)δppm: 0.91 (3H, d, J=6.9Hz), 2.14 (1H, dd, J=10.9Hz and 16.9Hz), 2.31–2.50 (3H, m), 2.67 (1H, dd, J=10.9Hz, and 16.9Hz), 2.83–2.92 (1H, m), 3.68 (3H, s)

EXAMPLE 4

(3S, 4R)-3-methoxycarbonyl-4-methylcyclopentanone

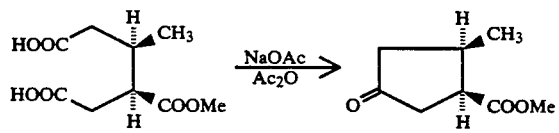

3.8 g of (3S, 4R)-3-methoxycarbonyl-4-methylhexane dicarboxylic acid and 1.1 g of sodium acetate were added to 18 ml of acetic anhydride, and the mixture was refluxed for one hour. The reaction mixture was cooled down to room temperature, and then allowed to stand for one hour at 5° C. The resulting precipitate was filtered off, and the filtrate was concentrated. To the residue was added ethyl acetate, and after the insoluble material was filtered off, the filtrate was concentrated. The residue was purified by distillation under a reduced pressure, and thus 2.23 g of the titled compound was obtained.

bp: 85° C./0.8 mmHg
$[\alpha]^{23}_D$: −19.0° (c=1.26, CHCl$_3$)
CI-MS m/z: 157 (M+1)$^+$
$^1$H-NMR(CDCl$_3$)δppm: 1.05 (3H, d, J=7.0Hz), 2.09-2.21 (1H, m), 2.29-2.47 (2H, m), 2.55-2.76 (2H, m), 3.16-3.26 (1H, m), 3.73 (3H, s)

EXAMPLE 5

(3S, 4R)-3-carboxy-4-methylcyclopentanone

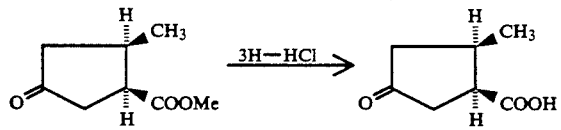

1.18 g of (3S, 4R)-3-methoxycarbonyl-4-methylcyclopentanone was added to 20 ml of 3N-hydrochloric acid, and the mixture was refluxed for 2 hours. The resultant mixture was cooled down to room temperature, and concentrated to dryness. The residue was purified by distillation under a reduced pressure, and thus 0.858 g of the titled compound was obtained.

bp: 140-142° C./0.5 mmHg
$[\alpha]^{23}_D$: −38.3° (c=1.9, CHCl$_3$)
CI-MS m/z: 143 (M+1)$^+$
$^1$H-NMR(CDCl$_3$)δppm: 1.14 (3H, d, J=7.0Hz), 2.12-2.25 (1H, m), 2.32-2.50 (2H, m), 2.58-2.82 (2H, m), 2.19-2.29 (1H, m)

EXAMPLE 6

(1S, 2R)-2-acetyl-1-methoxycarbonylcyclohex-4-ene

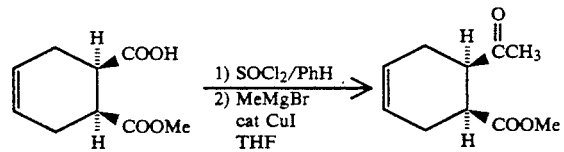

25 g of (1R, 2S)-2-methoxycarbonylcyclohex-4-ene-1-carboxylic acid and 40 ml of thionyl chloride were dissolved in 200 ml of dry benzene, and the mixture was refluxed for two hours. The solvent was distilled off under a reduced pressure, and to the residue was added ml of dried tetrahydrofuran. Further, 1.29 g of copper (I) iodide was added to the solution, which was cooled to −5° C, 182 ml of tetrahydrofuran solution of methylmagnesium bromide (0.82M) was added dropwise to the solution over a period of 1.5 hours. The solution was further stirred for one hour at the same temperature, and then 1N-hydrochloric acid was added. After the organic layer was separated, the water layer was extracted with ether. The organic layer was successively washed with 5% sodium thiosulfate solution, saturated sodium bicarbonate solution and brine, dried over anhydrous magnesium sulfate, and concentrated. The residue was subjected to silica gel column chromatography (ethyl acetate: hexane=15:85) to be purified, and thus 18.27 g of the titled compound was obtained.

$[\alpha]^{23}_D$: +18.9° (c=0.36, CHCl$_3$)
$^1$H-NMR(CDCl$_3$)δppm: 2.21 (1H, s), 2.30-2.65 (4H, m), 2.90 (1H, m), 3.08 (1H, m), 3.68 (3H, s), 5.65-5.75 (2H, br s)

EXAMPLE 7

(1S, 6R)-6-ethyl-1-methoxycarbonylcyclohex-3-ene

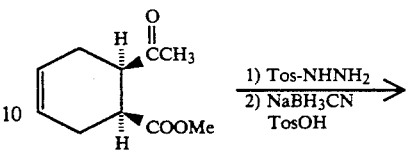

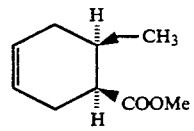

According to a manner similar to that of Example 2, 8.16 g of the mixture of the titled compound and 7% of trans-isomer thereof was obtained by use of 18.27 g of (1S, 2R)-2-acetyl-1-methoxycarbonylcyclohex-4-ene, and by purifying the resultant product with silica gel chromatography (ether:hexane=1:9)

$[\alpha]^{23}_D$: +34.2° (c=1.09, CHCl$_3$)
$^1$H-NMR(CDCl$_3$)δppm: 0.91 (3H, t, J=7.5Hz), 1.25-1.40 (2H, m), 1.70-2.40 (5H, m), 2.73 (1H, m), 3.67 (3H, s), 5.60-5.70 (2H, br s)

EXAMPLE 8

(3S, 4R)-3-methoxycarbonyl-4-ethylcyclopentanone

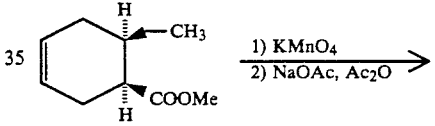

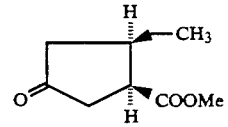

24 g of potassium permanganate is dissolved in 15 ml of water, and 8.08 g of (1S, 6R)-6-ethyl-1-methoxycarbonylcyclohex-3-ene was added to the solution over a period of 20 minutes. The mixture was stirred for 4 hours at room temperature, and then 6 g of potassium permanganate was further added, followed by 1 hour of stirring. Methanol was added to the mixture, and the insoluble material was filtered off. Concentrated hydrochloric acid was added to the filtrate such as to adjust the pH thereof at 2, and the filtrate was extracted with a mixed solvent of ethyl acetate - tetrahydrofuran (1:1). After concentration, to the residue were added 50 ml of acetic anhydride and 2.5 g of sodium acetate, and the mixture was refluxed for 1.5 hours. The mixture was cooled down to room temperature, and a mixed solvent of hexane - ether was added thereto. The insoluble material was filtered off, and the filtrate was concentrated. The residue was subjected to silica gel column chromatography (ether:hexane=1:2), thereby obtaining 3.99 g of titled compound.

$[\alpha]^{22}_D$: −76.4° (c=1.02, CHCl$_3$)
$^1$H-NMR(CDCl$_3$)δppm: 0.98 (3H, t, J=7.0Hz), 1.20-1.40 (1H, m), 1.40-1.60 (5H, m), 2.12-2.28 (1H, m), 2.28-2.50 (1H, m), 2.50-2.63 (1H, m), 3.25

(1H, m), 3.71 (3H, s)

EXAMPLE 9

(3S, 4R)-3-carboxy-4-methylcyclopentanone

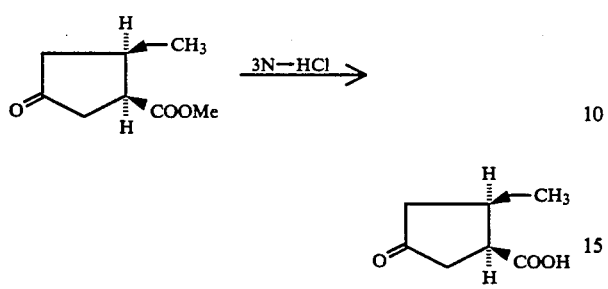

From 3.8 g of (3S, 4R)-3-methoxycarbonyl-4-ethyl-cyclopentanone, 2.96 g of the titled compound was obtained according to a manner similar to that of Example 5.

bp: 170°–180° C./0.4 mmHg
mp: 60°–61° C.
[α]$_D$: −98.5° (c=1.00, CHCl$_3$)
$^1$H-NMR (CDCl$_3$)δppm: 1.01 (3H, t, J=7.0Hz), 1.33–1.52 (1H, m), 1.52–1.72 (1H, m), 2.15–2.32 (1H, m), 2.32–2.53 (3H, m), 2.53–2.67 (1H, m), 3.27 (1H, m)

EXAMPLE 10

(1S, 2R)-2-acetyl-1-methoxycarbonylcyclohex-4-ene

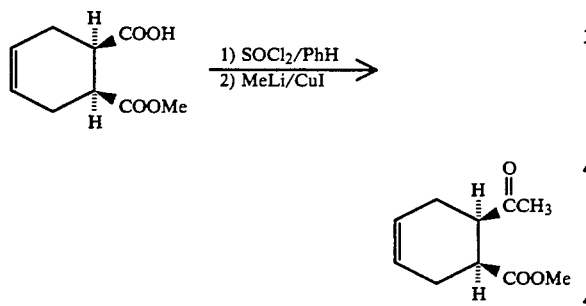

1 ml of dry ether was added to 141 mg of copper (I) iodide in a stream of nitrogen gas, and 1.35 ml of ether solution (1.1M) of a methyllithium was added dropwise to the mixture while cooling it by ice. The mixture was cooled down to −78° C. To the reaction mixture was added a solution of (1S, 2R)-2-chloroformyl-1-methoxycarbonylcyclohex-4-ene (50 mg) prepared by a method similar to that of Example 1 in ether (0.5 ml) at −70° C., and the mixture was stirred for one hour. After addition of methanol, the mixture was allowed to stand to return to room temperature, a saturated ammonium chloride solution was then added, and the mixture was stirred for 30 minutes. The reaction mixture was extracted with ether, dried over anhydrous magnesium sulfate, and concentrated. The residue was subjected to silica gel column chromatography (ethyl acetate:hexane=15:85) to be purified, and thus 35 mg of the titled compound was obtained.

$^1$H-NMR(CDCl$_3$)δppm: 2.21 (1H, s), 2.30–2.65 (4H, m), 2.90 (1H, m), 3.08 (1H, m), 3.68 (3H, s), 5.65–5.75 (2H, br s)

EXAMPLE 11

(1S, 2R)-2-benzoyl-1-methoxycarbonylcyclohex-4-ene

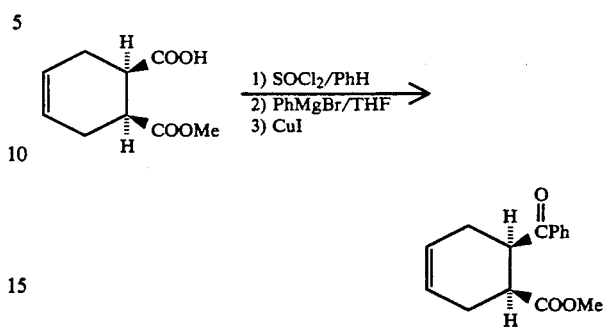

From 4.8 g of (1R, 2S)-2-methoxycarbonyl-1-carboxycyclohex-4-ene, 4.65 g of the titled compound was obtained by use of 20.5 ml of tetrahydrofuran solution (1.4M) of phenylmagnesium bromide in place of a tetrahydrofurane solution of methylmagnesium bromide according to a manner similar to that of Example 6.

yield: 73%
mp: 61°–62° C.
[α]$_D$: −21.8° (c=1.03, CHCl$_3$)
$^1$H-NMR(CDCl$_3$)δppm: 2.4–2.6 (3H, m), 2.65–2.80 (1H, m), 2.95–3.05 (1H, m), 3.63 (3H, s), 3.90–4.00 (1H, m), 5.60–5.80 (2H, m), 7.40–7.60 (3H, m), 7.86 (2H, d, J=6Hz)

EXAMPLE 12

(1S, 6S)-1-methoxycarbonyl-6-benzylcyclohex-4-ene

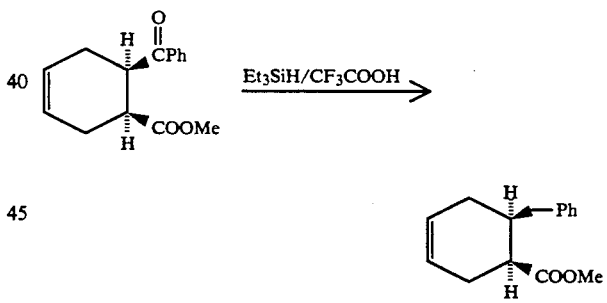

438 mg of (1S, 2R)-2-benzoyl-1-methoxycarbonylcyclohex-4-ene was dissolved in 2.5 ml of trifluoroacetic acid. To the solution, 2.5 ml of triethylsilyl hydride (Et$_3$SiH) was added at 50° C., and the solution was stirred for 30 minutes at the same temperature. After the solution was allowed to stand to return to room temperature, a saturated sodium bicarbonate solution was added, and the water layer was extracted with ether. Then, the organic layer was dried over anhydrous magnesium sulfate, concentrated, and the residue was subjected to silica gel column chromatography (ether:hexane=4:96), thereby obtaining 221 mg of the titled compound.

Yield: 54%
$^1$H-NMR (CDCl$_3$)δppm: 1.90–2.15 (2H, m), 2.20–2.80 (6H, m), 3.69 (3H, s), 5.60–5.75 (2H, m), 7.10–7.30 (5H, m)

EXAMPLE 13

(3S, 4R)-4-benzyl-3-methoxycarbonylcyclopentane

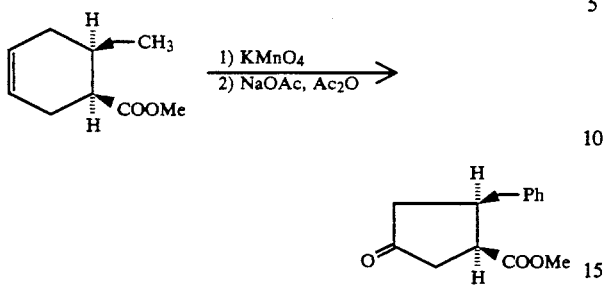

200 mg of (1S, 6R)-6-benzyl-1-methoxycarbonylcyclohex-4-ene was treated in a manner similar to that of Example 8, and the resultant was purified by silica gel column chromatography (ethyl acetate:hexane=2:8), thereby obtaining 20 mg of the titled compound.

$^1$H-NMR (CDCl$_3$)δppm: 2.0–2.7 (5H, m), 2.75–2.95 (2H, m), 3.23–3.33 (1H, m), 3.74 (3H, S), 7.10–7.35 (5H, m)

EXAMPLE 14

(1S, 6R)-6-bromomethyl-1-methoxycarbonylcyclohex-3-ene

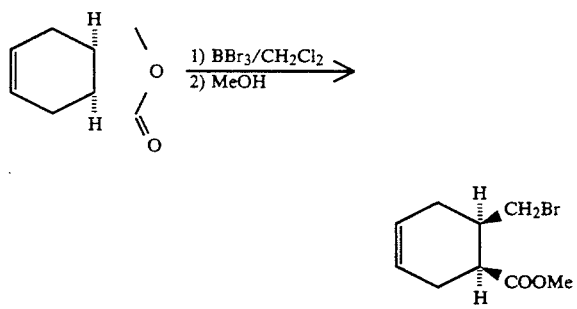

In a stream of nitrogen gas, 8.8 g of (3aR, 7aS)-1,3,3a,4,7,7a-hexahydroisobenzofuran-1-one was dissolved in 100 ml of dichloromethane, and 95 ml of dichloromethane solution of boron tribromide (1M-CH$_2$Cl$_2$ solution) was slowly added dropwise to the mixture while the mixture was being cooled by ice. Thereafter, the mixture was stirred for 24 hours at room temperature, the resultant mixture was cooled by ice, and then 60 ml of methanol was added extremely slowly thereto, in dropwise fashion. The mixture was refluxed for 3 hours. The resultant mixture was cooled by ice, and 50 ml of saturated sodium bicarbonate solution was added slowly thereto to separate the organic layer. The organic layer was washed with saturated sodium bicarbonate solution and water, and then dried over anhydrous magnesium sulfate. After filtration, the filtrate was concentrated, and the residue was distilled under a reduced pressure. Thus, 13.0 g of the titled compound was obtained.

Yield: 87.6%
bp: 92°–93° C./0.7 mmHg
[α]$^{25}$D: +34.6° (C=1.28, CHCl$_3$)

EXAMPLE 15

(1S, 6R)-6-bromomethyl-1-methoxycarbonylcyclohex-3-ene

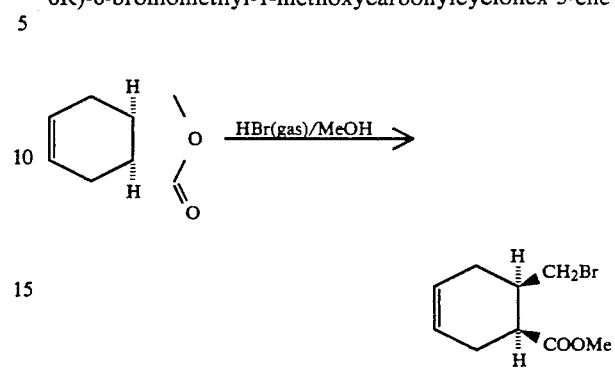

2.0 g of (3aR, 7aS)-1,3,3a,4,7,7a-hexahydroisobenzofuran-1-one was dissolved in 20 ml of methanol, and 14.0 g of hydrogen bromide gas was bubbled into the solution while being cooled by ice. The solution was stirred for 1.5 hours with ice-cooling, and water was added. The mixture was extracted three times with ether. The extracted solution was washed with saturated sodium bicarbonate solution, and dried over anhydrous magnesium sulfate. Then, filtration was performed, and the filtrate was concentrated under a reduced pressure. The residue was distilled under a reduced pressure, and thus 3.0 g of the titled compound was obtained.

Yield: 88%

EXAMPLE 16

(1S, 6R)-6-methoxycarbonyl-6-methylcyclohex-3-ene

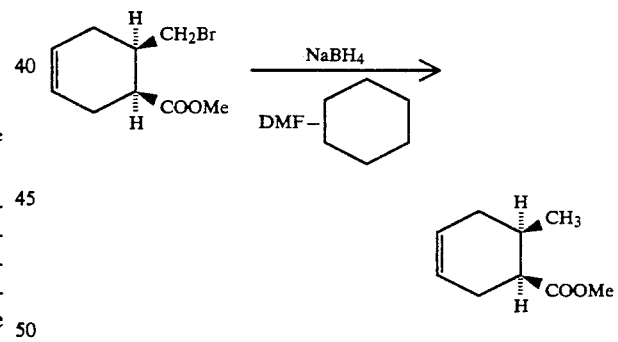

A solution of (1S, 6R)-6-bromomethyl-1-methoxycarbonylcyclohex-3-ene (5 g) dissolved in 150 ml of cyclohexane was added to a DMF (100 ml) solution of NaBH$_4$ (2.44 g), and the mixture was stirred for 6 hours at 70° C. The reaction mixture was cooled by ice, 150 ml of brine was added, and the water layer was extracted with cyclohexane. The combined cyclohexane layers were washed with brine. The organic layer was dried over anhydrous magnesium sulfate, and cyclohexane was distilled off under atmospheric pressure. The residue was purified by distillation under a reduced pressure, and thus 1.1 g of the titled compound was obtained.

Yield: 71%
bp: 92° C./25 mmHg
[α]$^{25}$D: +33.5° (C=1.56, CHCl$_3$)
CI-MS m/z: 155 (M+1)$^+$
(Comparative Examples)

COMPARATIVE EXAMPLE 1

(3aR, 7aS)-1,3,3a,4,7,7a-hexahydroisobenzofuran-1-one

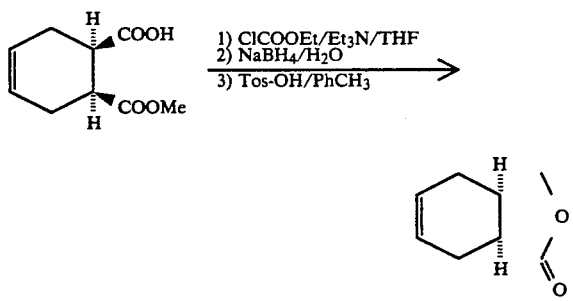

In a stream of nitrogen gas, 20 g of (1R, 2S)-2-methoxycarbonylcyclohex-4-ene-1-carboxylic acid was dissolved in 120 ml of dry tetrahydrofuran, and to the solution, was added 18.2 ml of triethylamine while the solution being cooled by ice. A dry tetrahydrofuran (40 ml) solution of ethyl chloroformate (12.4 ml) was slowly added dropwise to the mixture. While the mixture was being cooled by ice, the mixture was stirred for 2 hours. After filtration of the resulting triethylamine hydrochloride, the filtrate was added dropwise to a H₂O (100 ml) solution of NaBH₄ (10.3 g) with ice-cooling and the mixture was stirred for 2 hours at room temperature. Then, 2N-HCl was added to the mixture to adjust the pH thereof to 4–5, and THF was distilled off under a reduced pressure. The residue was extracted by ethyl acetate. The ethyl acetate layer was washed with saturated sodium bicarbonate solution and brine, and the organic layer was dried over anhydrous magnesium sulfate. After filtration, the filtrate was concentrated under a reduced pressure, and the residue was dissolved in 100 ml of toluene. 2.07 g of p-toluenesulfonic acid monohydrate was added to this solution, and the mixture was stirred for 5 hours at room temperature. The reaction mixture was washed with saturated sodium bicarbonate solution and brine. Then, the organic layer was dried over anhydrous magnesium sulfate, and after filtration, the filtrate was concentrated under a reduced pressure. The residue was distilled under a reduced pressure, and thus 9.35 g of the titled compound was obtained.

Yield: 62.1%
bp: 105°–106° C./2 mmHg
[α]²⁵D: −51.9° (C=1.72, CHCl₃)

COMPARATIVE EXAMPLE 2

(3R, 4R)-3-carboxy-4-methylcyclopentanone

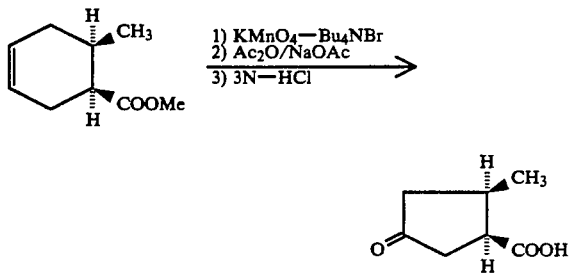

In a stream of nitrogen gas, 3.33 g of (1S, 6R)-1-methoxycarbonyl-6-methylcyclohex-3-ene was dissolved in 100 ml of cyclohexane, and the solution was added to a aqueous solution prepared by dissolving 13.5 g of potassium permanganate and 1.39 g of tetrabutylammonium bromide in 100 ml of H₂O. The mixture was vigorously stirred for 4 hours at room temperature. To the reaction mixture was added 10 g of sodium hydrogen-sulfate, and the precipitate was filtered off. After the cyclohexane layer of the filtration was separated, and the water layer was adjusted to have a pH of 3 by concentrated hydrochloric acid, the water layer was extracted by ethyl acetate-tetrahydrofuran (1:1). The cyclohexane layer and the extraction were combined, and dried over anhydrous magnesium sulfate. After filtration, the filtrate was concentrated under a reduced pressure. To the residue, 12.5 ml of acetic anhydride and 0.825 g of sodium acetate were added, and the mixture was stirred for 1 hour at 130° C. After being cooled by air, the precipitate was filtered off, and the filtrate was concentrated under a reduced pressure. The residue was taken up into ethyl acetate, and the insoluble material was filtered off, followed by concentration of the filtrate under a reduced pressure. The residue was distilled under a reduced pressure, and thus 1.35 g of (3S, 4R)-3-methoxycarbonyl-4-methylcyclopentanone was obtained.

Yield: 40.3%
bp: 85° C./0.8 mmHg 1.18 g of (3S, 4R)-3-methoxycarbonyl-4-methylcyclopentanone was dissolved in 20 ml of 3N-HCl, and the solution was refluxed for 2 hours. The reaction mixture was allowed to stand to return to room temperature, and concentrated. The residue was concentrated under a reduced pressure, and thus 1.05 g of the titled compound was obtained.

Yield: 98.2%

As described, the present invention is directed to a method of preparing a target compound [A, A'] from a compound [XII] as a starting material, via a novel intermediate compound [I], and according to the invention, the target compound can be obtained without having a problem of epimerization, by maintaining a desired configuration of the intermediate materials throughout the reaction steps.

We claim:

1. A method of producing a (1S, 6R)-6-halomethyl-1-carboxycyclohex-3-ene derivative represented by formula (X') below, comprising reacting (3aR, 7aS)-1,3,3a,4,7,7a-hexahydroisobenzofuran-1-one represented by formula (IX) with a halogenating agent in an inert solvent, followed by treating using a lower alcohol represented by R²OH or water,

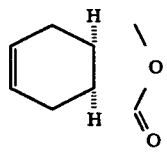 (IX)

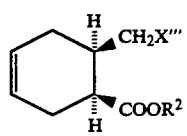 (X')

where R² is a hydrogen atom or a lower alkyl group, and X''' represents a halogen atom.

2. A method of producing a (1S, 6R)-6-halomethyl-1-carboxycyclohex-3-ene derivative represented by formula (X') below, comprising reacting (3aR, 7aS)-1,3,3a,4,7,7a-hexahydroisobenzofuran-1-one represented by formula (IX) with a halogenating agent in a lower alcohol solvent,

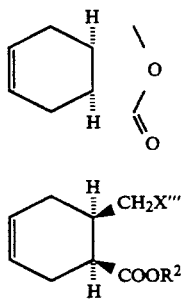
(IX)

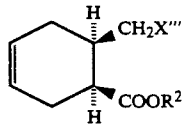
(X')

where $R^2$ is a hydrogen atom or a lower alkyl group, and X''' represents a halogen atom.

3. A method of producing a (1S, 6R)-6-halomethyl-1-carboxycyclohex-3-ene derivative, comprising hydrolyzing a compound represented by formula (X') when $R^2$ is a lower alkyl group, (X')

where $R^2$ is a hydrogen atom or a lower alkyl group and X''' is a halogen atom.

4. The method according to claim 1 wherein said lower alkyl group is an alkyl group having a carbon number of 1 to 4, which can be branched.

5. The method according to claim 2, wherein said lower alkyl group is an alkyl group having a carbon number of 1 to 4, which can be branched.

6. The method according to claim 3, wherein said lower alkyl group is an alkyl group having a carbon number of 1 to 4, which can be branched.

7. The method according to claim 4, wherein said lower alkyl group is a member selected from the group consisting of a methyl group, an ethyl group, a propyl group, an isopropyl group, a butyl group, an isobutyl group, a sec-butyl group, and a tert-butyl group.

8. The method according to claim 5, wherein said lower alkyl group is a member selected from the group consisting of a methyl group, an ethyl group, a propyl group, an isopropyl group, a butyl group, an isobutyl group, a sec-butyl group, and a tert-butyl group.

9. The method according to claim 6, wherein said lower alkyl group is a member selected from the group consisting of a methyl group, an ethyl group, a propyl group, an isopropyl group, a butyl group, an isobutyl group, a sec-butyl group, and a tert-butyl group.

10. The method according to claim 1, wherein said halogenating agent is a member selected from the group consisting of $SOCl_2$, $(COCl)_2$, $PCl_5$, $BBr_3$, $BCl_3BI_3$, $MeSi_3I$, and $MeSi_3Br$.

11. The method according to claim 10, wherein said halogenating agent is $BBr_3$.

12. The method according to claim 2, wherein said halogenating agent is a member selected from the group consisting of $SOCl_2$, $(COCl)_2$, $PCl_5$, $BBr_3$, $BCl_3$, $BI_3$, $MeSi_3I$, and $MeSi_3Br$.

13. The method according to claim 10, wherein said inert solvent is a member selected from the group consisting of dichloromethane, chloroform, and 1,2-dichloroethane.

14. The method according to claim 10, wherein said lower alcohol solvent is a member selected from the group consisting of methanol and ethanol.

15. The method according to claim 2, wherein said lower alcohol solvent is methanol and said halogenating agent is a member selected from the group consisting of HBr and HI gas.

16. The method according to claim 15, wherein said reacting is carried out at a temperature of $-20°$ C. to $40°$ C.

17. The method according to claim 16, wherein said reacting is carried out at room temperature.

* * * * *